US00PP28756P3

(12) United States Plant Patent
Ackerman et al.

(10) Patent No.: US PP28,756 P3
(45) Date of Patent: Dec. 12, 2017

(54) STRAWBERRY PLANT NAMED 'PE-7.2059'

(50) Latin Name: *Fragaria ananassa*
Varietal Denomination: PE-7.2059

(71) Applicant: PLANT SCIENCES, INC., Watsonville, CA (US)

(72) Inventors: Stephen M. Ackerman, Salinas, CA (US); Steven D. Nelson, Watsonville, CA (US); Michael D. Nelson, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 14/545,859

(22) Filed: Jun. 30, 2015

(65) Prior Publication Data

US 2017/0006747 P1 Jan. 5, 2017

(51) Int. Cl.
*A01H 5/08* (2006.01)

(52) U.S. Cl.
USPC ..... Plt./209

(58) Field of Classification Search
USPC ..... Plt./209
See application file for complete search history.

*Primary Examiner* — Keith Robinson
(74) *Attorney, Agent, or Firm* — Foley & Lardner LLP

(57) ABSTRACT

This invention relates to a new and distinct variety of strawberry plant named 'PE-7.2059'. This new strawberry plant named 'PE-7.2059' is primarily adapted to the growing conditions of the central coast of California, and is primarily characterized by its large fruit size that is red in color, conical in shape with medium to strong gloss and a calyx that tends to be raised; seeds that range from level with to above the surface; medium plant size, with foliage that lacks gloss and has medium to strong interveinal blistering; fruiting truss pubescence that is strong and held strongly outward; and stolons, stipules and fruiting trusses that all lack anthocyanin coloration.

4 Drawing Sheets

Latin name of the genus and species of the plant claimed: *Fragaria ananassa.*

Variety denomination: 'PE-7.2059'.

BACKGROUND OF THE INVENTION

The present invention relates to a new and distinct strawberry variety named 'PE-7.2059'. This new variety is a result of a controlled cross made in 2007 in an ongoing breeding program between strawberry selection designated 'PS-7625' (unpatented) and strawberry variety designated 'VALOR' (U.S. Plant Pat. No. 20,394). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, Calif. in the fall of 2009. After its selection, the new variety was asexually propagated by stolons in both San Joaquin County, Calif. and Siskiyou County, Calif. The new variety was extensively tested over the next several years in fruiting fields in Ventura County, Calif. This propagation has demonstrated that the combination of traits disclosed herein as characterizing the new variety are fixed and remain true to type through successive generations of asexual reproduction.

BRIEF SUMMARY OF THE INVENTION

'PE-7.2059' is primarily adapted to the climate and growing conditions of the central coast of California. The nearby Pacific Ocean provides the needed humidity and moderate temperatures to produce a strong vigorous plant and maintain fruit quality during the fall production months.

The following traits have been repeatedly observed and are determined to be unique characteristics of 'PE-7.2059', which in combination distinguish this strawberry plant as a new and distinct variety:

1. Large fruit size that is red in color, conical in shape with medium to strong gloss and a calyx that tends to be raised;
2. Seeds that range from level with to above the surface;
3. Medium plant size, with foliage that lacks gloss and has medium to strong interveinal blistering;
4. Fruiting truss pubescence that is strong and held strongly outward; and
5. Stolons, stipules and fruiting trusses have anthocyanin colorations that are absent or very weak.

The strawberry variety that is believed to be most closely related to the new variety 'PE-7.2059' is 'ARABELLA' (U.S. Plant Pat. No. 26,209). In side-by-side comparisons to the similar strawberry variety 'ARABELLA', 'PE-7.2059' differs by the following combination of characteristics as described in Table 1.

TABLE 1

COMPARISON WITH THE STANDARD VARIETY

| Characteristic | 'PE-7.2059' | 'ARABELLA' (U.S. Plant Pat. No. 26,209) |
|---|---|---|
| Fruit: size | Large (23.4 grams) | Medium (22.5 grams) |
| Fruit: L × W ratio | Slightly longer than broad | As long as broad |

TABLE 1-continued

| COMPARISON WITH THE STANDARD VARIETY | | |
|---|---|---|
| Characteristic | 'PE-7.2059' | 'ARABELLA' (U.S. Plant Pat. No. 26,209) |
| Fruit: insertion of achenes | Level with to above the surface | Level with to below the surface |
| Fruit: attitude of sepals | Ranges from outward to upward | Outward |
| Fruit: flavor | Good | Very good |
| Plant: size | Medium | Ranges from medium to large |
| Foliage: number of leaflets | Ranges from 3 to 4 | 3 |
| Foliage: shape in cross section | Strongly to slightly concave | Slightly concave to flat |
| Fruiting truss: length | Medium | Ranges from medium to long |
| Pedicel: attitude of hairs | Strongly outward | Upward |

For identification, a series of molecular markers have been determined for this new variety.

'PE-7.2059' differs from its parents, 'PS-7625' and 'VALOR', by the following combination of characteristics as described in Table 2.

TABLE 2

| COMPARISON WITH THE PARENT VARIETIES | | | |
|---|---|---|---|
| Characteristic | 'PE-7.2059' | 'PS-7625' | 'VALOR' |
| Type of bearing | Everbearing. | Summer bearing. | Everbearing. |
| Plant size | Medium. | Large. | Medium. |
| Fruit color | Medium red. | Medium red. | Ranges from medium to dark red. |
| Fruit flavor | Good. | Very good. | Good. |
| Disease reactions: | | | |
| angular leaf spot | Moderate. | Susceptible. | Susceptible. |

BRIEF DESCRIPTIONS OF THE PHOTOGRAPHS

The accompanying color photographs illustrate the overall appearance of typical specimens of the new strawberry variety 'PE-7.2059', at various stages of development as true as it is reasonably possible with color reproductions of this type. Color in the photographs may differ slightly from the color value cited in the botanical descriptions which accurately describe the color of 'PE-7.2059'. The depicted plant and plant parts of the new strawberry variety 'PE-7.2059' are between three and four months old. The photographs were taken in Ventura County, Calif.:

DETAILED BOTANICAL DESCRIPTION

Figure 1:
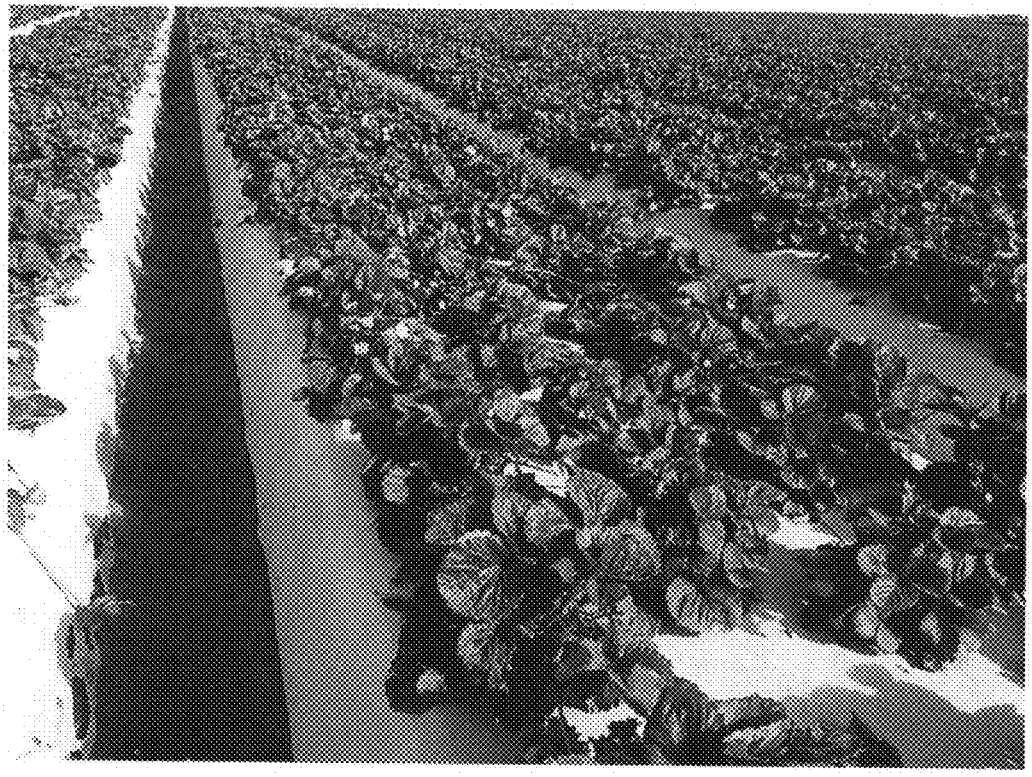
FIG. 1 shows typical fruiting field characteristics of 'PE-7.2059', taken in the month of October 2014.
Figure 2:
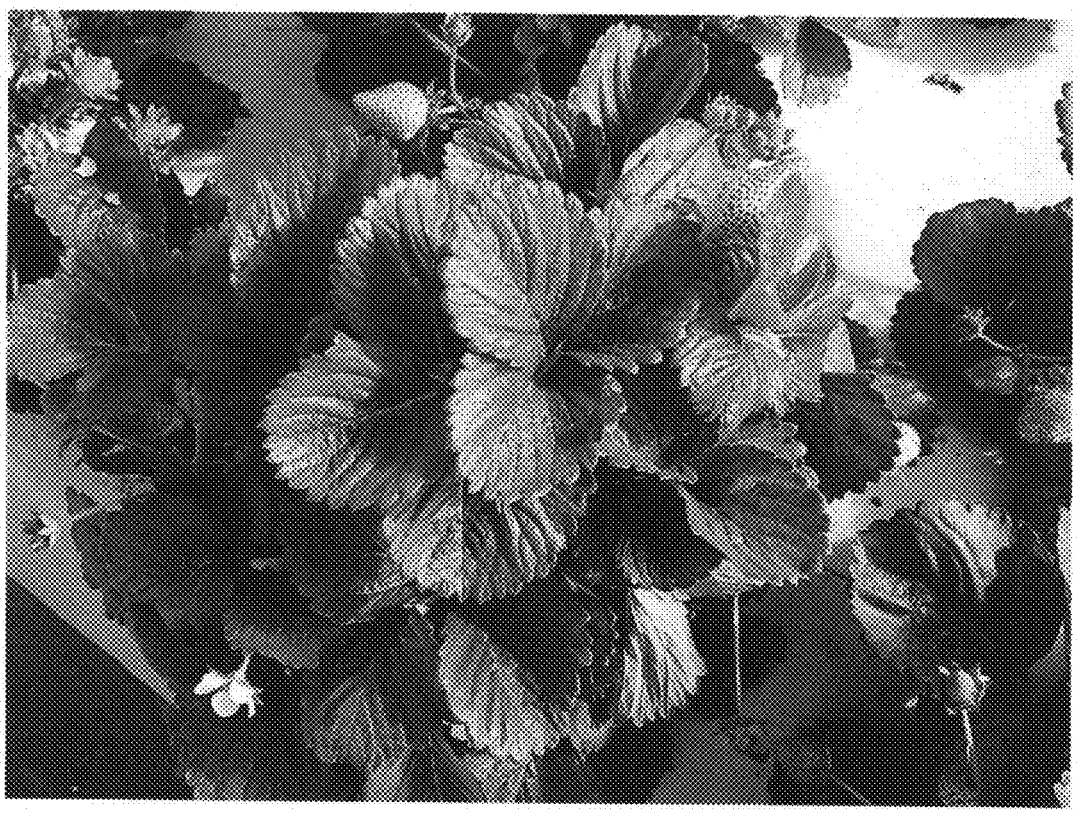
FIG. 2 shows a close-up view of the typical leaf structure of 'PE-7.2059', taken in the month of October 2014.
Figure 3:
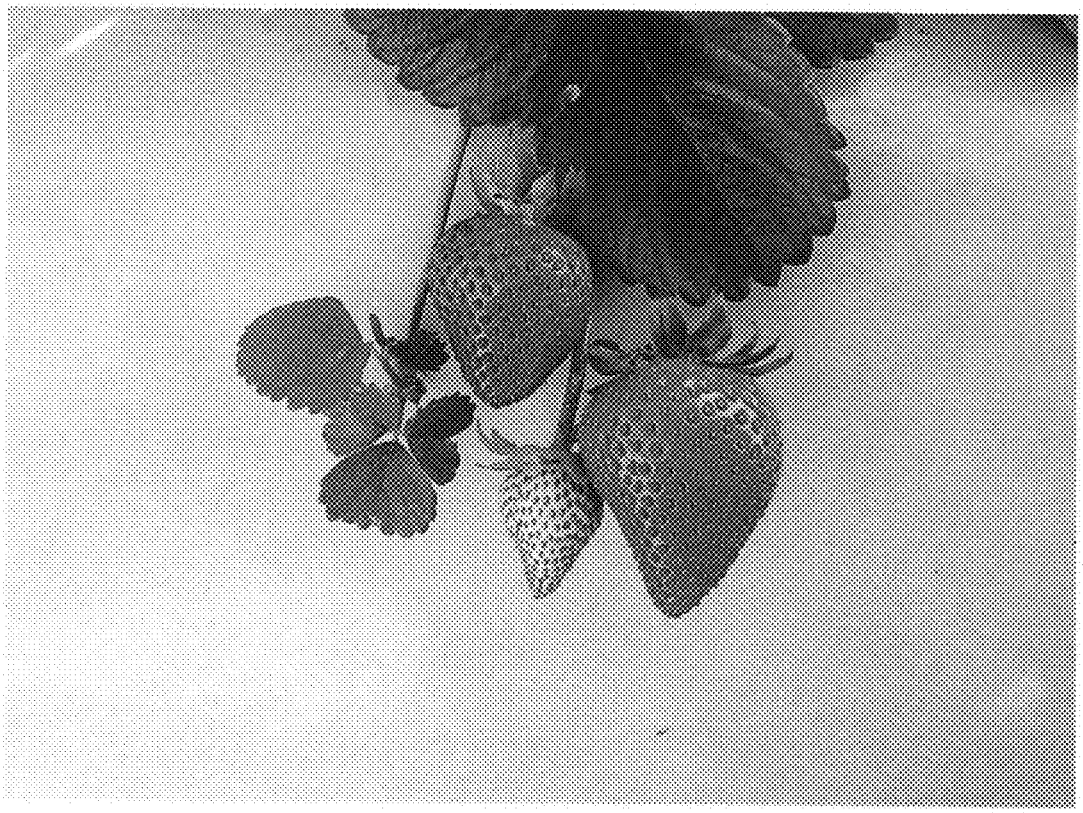
FIG. 3 shows typical mature and immature field fruit of 'PE-7.2059', taken in the month of October 2014.
Figure 4:
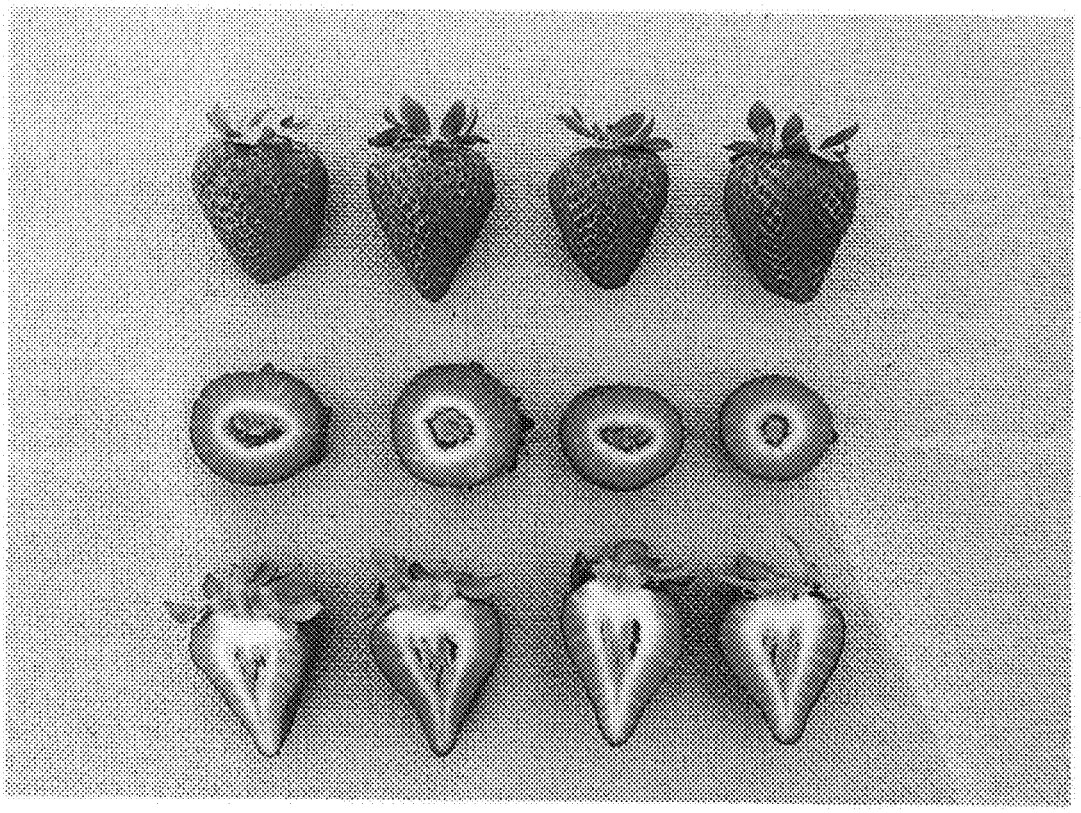
FIG. 4 shows typical internal and external mature fruit characteristics of 'PE-7.2059', taken in the month of October 2014.

The new variety 'PE-7.2059' has not been observed under all possible environmental conditions. The characteristics of the new variety 'PE-7.2059' may vary in detail, depending upon variations in environmental factors, including weather (temperature, humidity and light intensity), day length, soil type and location. In addition, the characteristics of any parental variety or comparison variety included in Tables 1 and 2 of the present invention may vary in detail, depending upon variations in environmental factors, including weather (temperature, humidity and light intensity), day length, soil type and location.

The aforementioned photographs, together with the following description of the new variety 'PE-7.2059', unless otherwise noted, are based on observations taken during the 2014 growing season in Ventura County, Calif. These measurements and ratings were taken from plants of 'PE-7.2059' dug from a low-elevation nursery located in San Joaquin County, Calif. during January 2014 and planted six months later in Ventura County, Calif. The approximate age of the observed plants is between three and four months. Yield observations including average weight and marketable yield, along with fruit quality characteristics including soluble solids, are averaged from four years of data collected from the 2011 through 2014 growing seasons. Flower measurements and characteristics are from secondary flowers unless otherwise noted. Fruit characteristics and measurements are from secondary fruit unless otherwise noted.

Where noted, color terminology follows The Royal Horticultural Society Colour Chart, London (2007).

The following characteristics describe fruit, plant, stolon, foliage, fruiting truss, flower, and pest and disease characteristics of the new strawberry 'PE-7.2059'.

Fruit characteristics:

*Color of mature fruit*.—RHS 46B (red).

*Color of internal flesh*.—RHS 45B (ranges from medium red to dark red).

*Color of core*.—RHS 44C (medium red).

*Length (cm)*.—4.6.

*Width (cm)*.—3.7.

*Size*.—Large.

*Length/width ratio*.—1.24 (slightly longer than broad).

*Calyx diameter (cm)*.—4.4.

*Season average weight (gm)*.—23.4.

*Achene color, shaded side*.—RHS 160A (greyed yellow group).

*Achene color, sun-exposed side*.—RHS 183B (greyed purple group).

*Achene weight (mg)*.—0.62.

*Achenes per berry*.—358.

*Season marketable yield (gm/plant)*.—628.

*Predominant shape*.—Conical.

*Difference in shape between primary and secondary fruit*.—Moderate.

*Band without achenes*.—Narrow.

*Evenness of surface*.—Even or very slightly uneven.

*Evenness of color*.—Even or very slightly uneven.

*Glossiness*.—Strong.

*Insertion of achenes*.—Ranges from level with surface to above surface.

*Position of calyx attachment*.—Ranges from level to raised.

*Attitude of sepals*.—Ranges from outward to upward.

*Size of calyx in relation to fruit diameter*.—Slightly larger.

*Adherence of calyx (when fully ripe)*.—Strong.

*Firmness of flesh*.—Medium.

*Distribution of red color of the flesh.*—Marginal and central.
*Hollow center expression.*—Ranges from weak to moderate.
*Flavor.*—Good.
*Soluble solids (% Brix).*—7.5.
*Time of first flowering.*—Medium, August in Ventura County, Calif.
*Time of first harvesting.*—Medium, September in Ventura County, Calif.
*Harvest period.*—Late September to mid December, in Ventura County, Calif.
*Harvest maturity.*—Mid season, November in Ventura County, Calif.
*Type of bearing.*—Fully remontant.

Plant characteristics:
*Height (cm).*—21.4.
*Spread (cm).*—32.3.
*Size.*—Medium.
*Habit.*—Upright.
*Density.*—Medium.
*Vigor.*—Strong.

Stolon characteristics:
*Color.*—RHS 146C (yellow green group).
*Anthocyanin coloration.*—RHS 181D (greyed red group).
*Anthocyanin intensity.*—Absent or very weak.
*Pubescence.*—Dense.
*Attitude of hairs.*—Slightly outward.
*Average quantity (nursery).*—Medium (ranges from 5 to 7 runners per square foot).
*Average diameter at bract (mm).*—3.9 (thick).

Terminal leaflet characteristics:
*Length (cm).*—7.9.
*Width (cm).*—7.5.
*Length/width ratio.*—1.05 (ranges from as long as broad to longer than broad).
*Shape of base.*—Obtuse.
*Shape of teeth.*—Rounded (crenate).
*Serrations per leaf.*—23.6.

Foliage characteristics:
*Color of upper surface.*—RHS N137D (medium green).
*Color of underside.*—RHS 147C (yellow green group).
*Number of leaflets.*—Ranges from 3 to 4.
*Size.*—Ranges from medium to small.
*Length (cm).*—12.5.
*Width (cm).*—14.5.
*Shape in cross section.*—Strongly to slightly concave.
*Interveinal blistering.*—Ranges from medium to strong.
*Leaf glossiness.*—Absent or weak.
*Leaf texture (upper surface).*—Medium to strong rugose.
*Leaf texture (underside).*—Medium to strong rugose.
*Leaf variegation.*—Absent.

Petiole characteristics:
*Color.*—RHS 146D (yellow green group).
*Length (cm).*—13.3.
*Diameter (mm).*—4.6.
*Attitude of hairs.*—Slightly outward.
*Frequency of bract leaflets.*—Occasionally.
*Bract leaflet size.*—Small (ranges from 1.5 to 2.0 square cm).
*Pubescence.*—Ranges from moderate to sparse.
*Petiolule color.*—RHS 146D (yellow green group).
*Petiolule length (mm).*—15.5.

Stipule characteristics:
*Color.*—RHS 146B (yellow green group).
*Anthocyanin coloration.*—Absent or very weak.
*Anthocyanin intensity.*—Absent or very weak.
*Length (mm).*—21.1.
*Width (mm).*—10.8.

Fruiting truss characteristics:
*Anthocyanin coloration.*—RHS 181D (greyed red group).
*Anthocyanin intensity.*—Absent or very weak.
*Length at maturity (cm).*—23.6.
*Position relative to foliage.*—Level with.
*Number of flowers.*—Medium (ranges from 25 to 30 per plant season long).
*Pedicel attitude of hairs.*—Strongly outward.
*Pubescence.*—Strong.
*Attitude at first pick.*—Prostrate.

Flower characteristics:
*Petal color.*—RHS NN 155C (white group).
*Sepal color.*—RHS 137A (green group).
*Receptacle color.*—RHS 148B (yellow green group).
*Anther color.*—RHS 13A (yellow group).
*Corolla diameter (mm).*—33.5 (ranges from medium to large).
*Calyx diameter (mm).*—35.2.
*Petal length (mm).*—12.3.
*Petal width (mm).*—12.1.
*Petal length/width ratio.*—1.01 (as long as broad).
*Petals/flower.*—6.8.
*Sepal length (mm).*—12.1.
*Sepal width (mm).*—6.3.
*Sepal length/width ratio.*—1.91.
*Sepals/flower.*—12.9.
*Size of calyx relative to corolla.*—Ranges from same size to larger.
*Size of inner calyx relative to outer calyx.*—Same.
*Relative position of petals (flowers with 5-6 petals).*—Overlapping.
*Stamen.*—Present.

Pest and disease reactions:
*Powdery mildew (Sphaerotheca macularis).*—Susceptible.
*Angular leaf spot (Xanthomonas fragaria).*—Moderate.
*Botrytis fruit rot (Botrytis cinerea).*—Moderately susceptible.
*Two-spotted spider mite (Tetranychus urticae).*—Moderately susceptible.

We claim:

1. A new and distinct strawberry plant named 'PE-7.2059', as herein described and illustrated by the characteristics set forth above.

* * * * *